United States Patent
Eyal et al.

(10) Patent No.: US 12,168,093 B2
(45) Date of Patent: Dec. 17, 2024

(54) MULTI-USERS MEDICAL CANNABIS DISPENSER

(71) Applicant: BUZZELET DEVELOPMENT AND TECHNOLOGIES LTD., Or-Akiva (IL)

(72) Inventors: Aharon Eyal, Or-Akiva (IL); Yuri Shadurin, Or-Akiva (IL); Meir Ariel, Or-Akiva (IL); Noa Raz, Or-Akiva (IL); Itai Rogel, Or-Akiva (IL); Carmi Raz, Or-Akiva (IL)

(*) Notice: Subject to any disclaimer, the term of this patent is extended or adjusted under 35 U.S.C. 154(b) by 831 days.

(21) Appl. No.: 17/275,214

(22) PCT Filed: Sep. 11, 2019

(86) PCT No.: PCT/IB2019/057660
§ 371 (c)(1),
(2) Date: Mar. 11, 2021

(87) PCT Pub. No.: WO2020/053787
PCT Pub. Date: Mar. 19, 2020

(65) Prior Publication Data
US 2022/0040421 A1 Feb. 10, 2022

Related U.S. Application Data

(60) Provisional application No. 62/729,812, filed on Sep. 11, 2018.

(51) Int. Cl.
*A61M 15/00* (2006.01)
*A61K 31/05* (2006.01)
(Continued)

(52) U.S. Cl.
CPC .......... *A61M 15/0066* (2014.02); *A61K 31/05* (2013.01); *A61K 31/352* (2013.01);
(Continued)

(58) Field of Classification Search
CPC .......... A61M 15/0066; A61M 15/0003; A61M 15/0021; A61M 15/0068; A61M 15/0083;
(Continued)

(56) References Cited

U.S. PATENT DOCUMENTS 3,348,735 A * 10/1967 Haltzman ............... G07F 13/08
222/2
4,933,873 A *  6/1990 Kaufman ............... G16H 40/67
600/300

(Continued)

FOREIGN PATENT DOCUMENTS

CA       2804124 A1 *  1/2012 ............. A61B 5/117
CN    101917956 A  * 12/2010 ............. G07F 11/44
(Continued)

OTHER PUBLICATIONS

CN 101917956 A description translation accessed Dec. 20, 2023 (Year: 2023).*

(Continued)

*Primary Examiner* — Margaret M Luarca
*Assistant Examiner* — Kira B Daher
(74) *Attorney, Agent, or Firm* — AlphaPatent Associates Ltd.; Daniel J. Swirsky (57) ABSTRACT

Provided is a multi-users cannabis dispenser comprising: a vessel comprising at least two compartments, each compartment configured to contain at least one cannabis composition comprising at least one active component; at least one dispensing unit associated with said at least one compartment, said dispensing unit configured to controllably release from said compartments a metered dose of said composition contained therein; a control unit comprising a data input unit configured to receive data relating to a specific user, data indicating a metered dose of one or more said cannabis compositions to be administered to said specific user and/or (Continued)

to receive data relating to a specific cannabis composition, data indicating a metered dose of said specific composition to be administered to said specific user and configured to control the dispensing unit to release at least one said metered dose. Further provided are methods of use of the multi-users cannabis dispenser.

16 Claims, 5 Drawing Sheets

(51) Int. Cl.
*A61K 31/352* (2006.01)
*A61M 11/04* (2006.01)

(52) U.S. Cl.
CPC ...... *A61M 11/041* (2013.01); *A61M 15/0003* (2014.02); *A61M 15/0021* (2014.02); *A61M 15/0068* (2014.02); *A61M 2205/18* (2013.01); *A61M 2205/3553* (2013.01); *A61M 2205/581* (2013.01); *A61M 2205/583* (2013.01); *A61M 2205/609* (2013.01); *A61M 2205/84* (2013.01); *A61M 2230/005* (2013.01); *A61M 2230/04* (2013.01); *A61M 2230/10* (2013.01); *A61M 2230/201* (2013.01); *A61M 2230/205* (2013.01); *A61M 2230/50* (2013.01)

(58) Field of Classification Search
CPC .............. A61M 11/041; A61M 11/042; A61M 2205/18; A61M 2205/3553; A61M 2205/581; A61M 2205/583; A61M 2205/609; A61M 2205/84; A61M 2205/276; A61M 2205/3592; A61M 2205/80; A61M 2205/10; A61M 2205/3368; A61M 2205/364; A61M 2205/502; A61M 2205/52; A61M 2205/8206; A61M 2230/005; A61M 2230/04; A61M 2230/10; A61M 2230/201; A61M 2230/205; A61M 2230/50; A61M 2230/30; A61M 2230/06; A61M 11/007; A61M 2209/10; A61M 2250/00; A61M 2202/0007; A61M 5/16827; A61K 31/05; A61K 31/352; A61K 31/658; G16H 20/13; G16H 20/10; G16H 10/60; A61B 5/4848; Y02A 90/10; A24F 40/30; A61J 3/00; G07F 13/08; G07F 9/105; G07F 17/0092
See application file for complete search history.

(56) References Cited

U.S. PATENT DOCUMENTS

| 5,848,593 | A  | * | 12/1998 | McGrady ............... G16H 20/13 128/897 |
| 7,467,093 | B1 | * | 12/2008 | Newton ............. G07F 17/0092 705/2 |
| 7,654,261 | B1 | * | 2/2010  | Rockhold ............. A61B 50/13 128/202.13 |
| 7,844,363 | B1 | * | 11/2010 | Mehdizadeh .......... G07F 9/026 700/232 |
| 2003/0216831 | A1 | * | 11/2003 | Hart ...................... G16H 15/00 700/235 |
| 2005/0042172 | A1 |   | 2/2005  | Whittle |
| 2006/0058724 | A1 | * | 3/2006  | Handfield ............... G07F 9/026 221/9 |
| 2015/0296879 | A1 |   | 10/2015 | Emarlou |
| 2016/0155127 | A1 | * | 6/2016  | Hartman ................ H04N 5/772 705/18 |
| 2016/0166625 | A1 | * | 6/2016  | Postma .................. G07F 13/10 424/725 |
| 2016/0166786 | A1 |   | 6/2016  | Kinzer |
| 2016/0325055 | A1 |   | 11/2016 | Cameron |
| 2016/0337362 | A1 |   | 11/2016 | Cameron |
| 2018/0228990 | A1 | * | 8/2018  | Cole ................. A61M 15/0086 |
| 2018/0301211 | A1 | * | 10/2018 | Pappas .................... A61B 5/163 |
| 2019/0062144 | A1 | * | 2/2019  | Greenbaum ........ G07F 17/0092 |
| 2019/0114685 | A1 | * | 4/2019  | Postrel .............. G06Q 30/0607 |

FOREIGN PATENT DOCUMENTS

| WO | 2003097141 A2 | 11/2003 |
| WO | 2012006125 A1 | 1/2012 |
| WO | 2019100160 A1 | 5/2019 |

OTHER PUBLICATIONS

International Preliminary Report on Patentability for PCT/IB2019/057660 issued Mar. 9, 2021.
International Search Report for PCT/IB2019/057660 mailed Dec. 12, 2019.
EP 19859282, Supplementary European Search Report dated May 20, 2022.

* cited by examiner

MULTI-USERS MEDICAL CANNABIS DISPENSER

FIELD OF THE INVENTION

The field of art to which this invention generally pertains is medical use of cannabis, and specifically to a cannabis dispenser for use by multiple users.

BACKGROUND OF THE INVENTION

*Cannabis* has been used for medical purposes and for relief of symptoms for thousands of years, and in the western world since the 18$^{th}$ century. Since then and until the present day, the most common route of administration has been by smoking. Due to the known disadvantages of smoking, other routes of administration are desired. This is particularly true for use in public places, and even more so, for treating patients in hospitals and nursing homes.

One of the main alternatives to smoking as a method of administration is the use of vaporizers, which have the advantage of rapidly providing beneficial effects without the health challenges and problems associated with smoking. Vaporizers have been known for many years, and a variety of devices are currently commercially available. Yet, the majority of users still prefer smoking, suggesting that the available vaporizers do not accomplish the desired objectives.

A disadvantage of vaporizers is the need for sophisticated and expensive versions of the apparatus for well-controlled medical treatment and for high yield of cannabis utilization. Another challenge is related to the complexity of operating such sophisticated equipment, particularly in the case of children, elderly and handicapped or sick patients. Hospitals and nursing homes treating multiple cannabis users face additional difficulties related to the need to store a relatively large amount of cannabis serving s of different compositions, doze size and delivery method. Other difficulties are related to the need for tailoring the serving properties to the particular need of the various patients and other challenges faced by the caregivers.

SUMMARY OF THE INVENTION

According to an aspect of some embodiments of the present invention, there is provided a multi-users cannabis dispenser comprising
(i) a vessel comprising at last two compartments, each compartment being configured to contain therein at least one cannabis composition comprising at least one active component;
(ii) at least one dispensing unit associated with said at least one compartment, wherein said dispensing unit is configured to controllably release from said compartments a metered dose of said composition contained therein;
(iii) a control unit comprising a data input unit configured to receive data relating to a specific user, data indicating a metered dose of one or more said cannabis compositions to be administered to said specific user and/or configured to receive data relating to a specific cannabis composition, data indicating a metered dose of said specific composition to be administered to said specific user and configured to control the dispensing unit to release at least one said metered dose.

According to an embodiment, said dispensing unit is configured to dispense said at least one metered dose of cannabis to each of said multiple users substantially simultaneously.

According to an embodiment, said at least one cannabis composition is provided in a selected dose size and/or selected delivery form.

According to an embodiment, the multi-users cannabis dispenser further comprises at least one cannabis activation unit, wherein said cannabis activation unit is configured to activate said at least one active component in said released metered dose to a selected activated form for said specific user.

According to an embodiment, said cannabis activation unit comprises a heating element, wherein said released metered dose is heated by said heating element and wherein said control unit is further configured to control said heating element to vaporize at least a portion of said at least one active component of said metered dose of said cannabis composition according to selected vaporizing parameters, wherein a vapor of said active component is formed and optionally provided to said specific user.

According to an embodiment, said cannabis activation unit comprises a spraying element wherein said released metered dose is in a liquid form and said spraying unit is configured to spray at least a portion of said at least one active component of metered dose and wherein said control unit is further configured to control said spraying element wherein a spray of said active component is formed and optionally provided to said specific user.

According to an embodiment, said activation unit comprises a combustion element, wherein said metered dose is combusted by said combustion element and wherein said control unit is further configured to control said combustion element to vaporize at least a portion of said at least one active component of said metered dose of said cannabis composition at selected vaporizing parameters, wherein a vapor of said active component is formed and optionally provided to said specific user.

According to an embodiment, said data input unit is configured to receive data comprising at least one user parameter selected from the group consisting of user identity data, user personal data, user physical data, user medical data, user licensing data, user billing data and user parameter data or combinations thereof.

According to an embodiment, the multi-users cannabis dispenser further comprises at least one unit selected from the group consisting of:
(i) a user feedback unit configured to receive feedback data of a user, wherein said feedback data comprises at least one selected from the group consisting of symptom severity prior to use, symptom severity after use and adverse effect of use.
(ii) a user-billing unit configured to provide a bill related to a user; and
(iii) at least one user physical parameter reader configured to obtain a physical parameter from a user,
wherein said dispenser optionally further comprises at least one data output unit configured to send data from at least one unit a) to c) to said control unit.

According to an embodiment, the multi-users cannabis dispenser further comprises an authorization users limiting mechanism.

According to an embodiment, said at least one cannabis composition comprises at least one selected from the group consisting of a cannabinoid, a solution of a cannabinoid in a solvent, a cannabis plant material, a cannabis extract, at least one terpene, a solution of said extract in a solvent and combinations thereof.

According to an embodiment, said metered dose is selected from the group consisting of tablets, suppositories, capsules, vaporizer cartridges, vaporizer tablets, aerosol cartridges, cigarettes, topicals, patches, oil droplets, edibles, beverages and combinations thereof.

According to an embodiment, each of said at least two compartments is independently configured to contain a dose form of a cannabis composition selected from the group consisting of tablets, suppositories, capsules, vaporizer cartridges, vaporizer tablets, aerosol cartridges, cigarettes, topicals, patches, oil droplets, edibles, beverages and combinations thereof.

According to an embodiment, said control unit is configured to control said heating element according to at least one selected from the group of a data input comprising user medical and/or personal data, said metered dose data or both.

According to an embodiment, said user medical data comprises at least one selected from the group consisting of user medical condition, user medical parameters data, and user medication protocol.

According to an embodiment, said received data relating to a specific user is a property or sensed parameter selected from the group consisting of age, gender, blood pressure, blood oxygen saturation level, heart rate, blood glucose concentration, user pain sensitivity, user anxiety level, user temperature, user photograph, user video recording, user EEG data, and combinations thereof.

According to an embodiment, said received data relating to a specific cannabis composition comprises at least one of selected cannabis batch ID, selected cannabis composition, selected cannabis dose, selected delivery form, selected activation unit, selected heating profile, selected dispensing date and time of dispensing and combinations thereof.

According to an embodiment, said control unit is configured to communicate with at least one selected from the group consisting of a supervisor and a medical server, wherein said supervisor and/or said medical server can receive data and operate said control unit.

According to an embodiment, the multi-users cannabis dispenser further comprises an additive input unit, configured to provide a selected additive in a selected amount to be combined with said metered dose.

According to an embodiment, said additive comprises at least one herbal preparation.

According to an embodiment, said additive comprises at least one terpene.

According to an embodiment, the multi-users cannabis dispenser further comprises at least one selected from the group consisting of a power storage unit, a display, a voice notification and voice alarm unit, at least one mouth piece, a mouth piece sterilizer, an inhaling mask, a flowmeter, a metered dose content monitor optionally connected to a data output unit and combinations thereof.

According to an aspect of some embodiments of the present invention, there is provided a method for dispensing cannabis to multiple users, the method comprising:
(i) providing a multi-user cannabis dispenser as disclosed herein,
(ii) introducing into each of said at least two compartments of said dispenser at least one cannabis composition comprising at least one active-component; and
(iii) providing to said data input unit at least one data input relating to a specific user, wherein said data input is selected from the group consisting of user identity data, user personal data, user medical data, user licensing data, user billing data and user parameter data,
wherein said control unit receives said data input relating to a specific user, data indicating a metered dose of one or more said cannabis compositions to be administered to said specific user and/or configured to receive data relating to a specific cannabis composition, data indicating a metered dose of said specific composition to be administered to said specific user and controls said dispensing unit to release at least one said metered.

According to an embodiment, said dispensing cannabis to each of said multiple users is carried out substantially simultaneously.

According to an embodiment, at least one of the data of the provided multi-user cannabis dispenser, metered dose, user parameters prior to use, user parameters after use, user feedback and user adverse effects via said data output unit is shared with a supervisor and said supervisor controls the multi-user cannabis dispenser operation.

According to an embodiment, said multi-users cannabis dispenser further comprises at least one cannabis activation unit comprising a heating element and wherein said control unit is further configured to control said heating element, the method further comprising:
(i) providing to said control unit data for selected vaporizing parameters whereby said control unit activates said heating element; and
(ii) vaporizing at least a portion of said at least one active component of said metered dose of said cannabis composition, whereby vapors of said active component are formed and delivered to a user,
wherein said vaporizing is controlled by said provided data.

According to an embodiment, said multi-users cannabis dispenser further comprises at least one cannabis activation unit comprising a spraying element and wherein said control unit is further configured to control said spraying element, the method further comprising:
(i) providing to said control unit data for selected spraying parameters, wherein said spraying element is activated; and
(ii) spraying at least a portion of said at least one active component of said metered dose of said cannabis composition, whereby a spray of said active components is formed and delivered to a user,
wherein said spraying is controlled by said provided data.

According to an embodiment, said multi-users cannabis dispenser further comprises at least one cannabis activation unit comprising a combustion element and wherein said control unit is further configured to control said combustion element, the method further comprising:
(i) providing to the control unit data selected combustion parameters, wherein said combustion element is activated; and
(ii) combusting at least a portion of said at least one active component of said metered dose of said cannabis composition, whereby a vapor of said active component is formed and delivered to a user,
wherein said combusting is controlled by said provided data.

According to an embodiment, the method further comprises billing said user according to said metered dose dispensed.

According to an embodiment, said control unit of said multi-users cannabis dispenser communicates with a supervisor or a central medical records processing device.

According to an embodiment, said dispenser further comprises an additive input unit configured to provide a selected additive in a selected amount, the method further comprising introducing said selected additive to said additive unit whereby said selected additive is added to said metered dose.

According to an embodiment, said additive comprises at least one herbal preparation.

According to an embodiment, said additive comprises at least one terpene.

According to an embodiment, said metered dose is provided in a delivery form selected from the group consisting of tablets, suppositories, capsules, vaporizer cartridges, vaporizer tablets, aerosol cartridges, cigarettes, topical, patches, oil droplets, edibles, beverages and combinations thereof.

According to an embodiment, said metered dose comprises at least one selected from the group consisting of at least one of a cannabinoid, a solution of a cannabinoid in a solvent, a cannabis plant material, a cannabis extract, at least one of a terpene, a solution of said extract in a solvent and combinations thereof.

DETAILED DESCRIPTION OF THE INVENTION

The particulars shown herein are by way of example and for purposes of illustrative discussion of the various embodiments of the present invention only and are presented in the cause of providing what is believed to be the most useful and readily understood description of the principles and conceptual aspects of the invention. In this regard, no attempt is made to show details of the invention in more detail than is necessary for a fundamental understanding of the invention, the description making apparent to those skilled in the art how the several forms of the invention may be embodied in practice.

The present invention will now be described by reference to more detailed embodiments. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities of components, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

Additional advantages of the invention will be set forth in part in the description, which follows, and in part will be obvious from the description, or may be learned by practice of the invention. It is to be understood that both the foregoing general description and the following detailed description are exemplary and explanatory only and are not restrictive of the invention, as claimed.

Unless indicated otherwise, percent is weight percent and ratio is weight/weight ratio.

According to an aspect of some embodiments of the present invention, provided is a multi-users cannabis dispenser comprising (i) a vessel comprising at least two compartments, each compartment being configured to contain therein at least one cannabis composition comprising at least one active component; (ii) at least one dispensing unit associated with said at least one compartment, wherein said dispensing unit is configured to controllably release from said compartments a metered dose of said composition contained therein; (iii) a control unit comprising a data input unit configured to receive data relating to a specific user, data indicating a metered dose of one or more said cannabis compositions to be administered to said specific user and/or configured to receive data relating to a specific cannabis composition, data indicating a metered dose of said specific composition to be administered to said specific user and configured to control the dispensing unit to release at least one said metered dose.

According to an embodiment, said dispenser comprises data storage unit, configured to store at least one of data received via said data input unit, data received via user feedback unit, data received via billing unit and data received from said physical parameter reader. According to an embodiment, said data storage unit is configured to share data with said control unit, said data output unit or both.

According to an embodiment, said dispensing unit is configured to dispense cannabis metered doses to at least one user. According to an embodiment, said dispensing unit is configured to dispense cannabis metered doses to multiple users, e.g. at least 3, at least 5, at least 10 or at least 15. According to an embodiment, said dispensing unit is configured to dispense said at least one metered dose of cannabis to each of said multiple users substantially simultaneously. According to an embodiment, the same metered dose is dispensed to each of the multiple users. According to an alternative embodiment, different metered doses are delivered to each of at least two different users.

According to an embodiment, said user is a human. According to an embodiment, said user is a non-human animal. According to an embodiment, said user is of any age, for example, an infant, a child, an adult, such as an elderly person. According to an embodiment, said user is ill. According to an embodiment, said user is healthy. According to an embodiment, said user is hospitalized. According to an embodiment, said user is being treated at a first aid center. According to an embodiment, said user is disabled or handicapped.

According to an embodiment, said vessel is configured to contain multiple cannabis compositions comprising at least one active component, within said at least two compartments. According to an embodiment, said vessel is configured to contain multiple metered doses of cannabis compositions, within said at least two compartments for example, at least 5, at least 10, at least 50, at least 100, at least 150, at least 200, at least 250, or at least 300. As used herein, the term "selected dose" or "metered dose" refers to the content of active components in said metered dose of cannabis. According to an embodiment, the metered dose dispense to a user includes the selected content of cannabis compositions comprising active components that fit such user treatment profile.

According to an embodiment, said vessel is built similarly to a safe to avoid unauthorized use. According to an embodiment, said vessel is configured to be locked. According to an embodiment, said dispenser weighs more than 1 kilogram (Kg), more than 3 Kg, more than 5 Kg or more than 10 Kg. Any shape of vessel is suitable. According to various embodiments, said vessel is shaped as a square, a cylinder, a pyramid, a ball or any combination thereof. According to an embodiment, the largest dimension of said vessel is greater than 40 centimeters (cm), greater than 60 cm, greater than 80 cm or greater than 100 cm. According to an embodiment, said dispenser is too large and/or too heavy to be hand-held by an adult user having normal physical strength. According to an embodiment, said dispenser is fixed to a selected location, e.g. to a wall. According to an alternative embodiment, said dispenser is portable, e.g. it has wheels and could be moved between locations and between users.

According to an embodiment, said dispenser is operatable by said user. As used herein, the term "user" is intended to refer to a recipient of a metered dose of cannabis. According to an embodiment, said dispenser is operatable by an operator other than the user. According to an embodiment, said operator is a caregiver, e.g. selected from physicians, nurses, therapists, pharmacists, family members and non-professional care givers. As used herein, operating may include filling cannabis compositions into said compartments, selecting the metered dose, operating the dispenser and operating a unit such as a vaporizing unit and a spraying unit. According to an embodiment, said operating requires a special license or a special training. According to an embodiment, said operating is too complex for said user technologically or the user is too sick to properly operate said dispenser and therefore depends on a caregiver.

According to an embodiment, said vessel comprises at least two compartments, which compartments are configured to contain cannabis compositions comprising active-components of selected cannabis compositions, of selected dose size and of selected delivery form. According to an embodiment, said vessel comprises at least 3 compartments, at least 6, at least 9, at least 12, or at least 15 compartments. According to an embodiment, each compartment comprises cannabis compositions characterized by having the same composition, same dose size and/or same delivery form.

As used herein, the term "active component" refers to materials or ingredients which have a physiological effect on an animal, including a human, and is intended to include both components which are present in a composition in activated form and components which require an activation step. Such components include compounds found in cannabis plant material in its natural or processed stages, including cannabinoids, terpenes and flavonoids. The term is not limited to components of specific activity or to components of explained activity. According to an embodiment, said cannabinoids are selected from the group consisting of tetrahydrocannabiniol in acid or decarboxylated form (THCa or THC, respectively), cannabidiol in acid or decarboxylated form (CBDa or CBD, respectively), cannabigerol in acid or decarboxylated form (CBGa or CBG, respectively), cannabichromene in acid or decarboxylated form (CBCa or CBC, respectively) tetrahydrocannabivarin in acid or decarboxylated form (THCVa or THCV, respectively), Cannabidivarin in acid or decarboxylated form (CBDVa or CBDV respectively), Cannabinol in acid or decarboxylated form (CBNa or CBN, respectively), Cannabicyclol in acid or decarboxylated form (CBLa or CBL, respectively), Cannabivarin in acid or decarboxylated form (CBVa or CBV, respectively) and combinations thereof. According to an embodiment, said terpenes are selected from the group consisting of pinene, limonene, linalool, caryophyllene, caryophyllene oxide, myrcene, humulene, borneol, eucalyptol, terpineol, nerolidol, phytol, geraniol, bisabolol, camphene, amyrin, thujone, citronellol, pulegone, cycloartenol, cymene, sabinene, carene, terpinene, fenchol, isopulegol, guaiol, phellandrene, eudesmol, ocimene, cardinol, elemene, friedelin, carvacrol, eugenol, camphor, menthol, iso-menthone, neral, gerial, viridiflorol, germacrene, thymol, Menth-2-en-1-ol, farensol, carotol, myrtenol, isomers thereof and combinations thereof. According to an embodiment, said flavonoids are selected from the group consisting of quercetin, luteolin, kaempferol, apigenin, cannaflavin A, cannaflavin B, cannaflavin C, β-sitosterol, vitexin, isovitexin, orientin and combinations thereof-. According to an embodiment, said metered dose composition is selected from the group consisting of at least one of a cannabinoid, a solution of a cannabinoid in a solvent, a cannabis plant material, a cannabis extract, at least one of a terpene, at least one of an herbal extract, a solution of said extract in a solvent and combinations thereof. According to an embodiment, said solvent is selected from the group consisting of terpenes, ethylene glycol, propylene glycol, ethanol and combinations thereof. As used herein, the term cannabis plant material refers to any part of the cannabis plant. According to an embodiment said cannabis plant material is derived from a cannabis inflorescence (or bud). As used herein, the term extract refers to the product of bringing a solvent with cannabis plant material, as such, or after the removal of at least part of the solvent.

As used herein, the term "selected cannabis compositions" refers to the compounds contained in a metered dose of cannabis, including active components, and to the amounts therein of each compound. According to an embodiment, a metered dose contains at least 0.1 milligram (mg) cannabinoids, at least 0.5 mg, at least 1 mg, at least 5 mg, at least 10 mg, at least 15 mg or at least 20 mg. As used herein, the term "selected delivery form" refers to the form of the metered dose in which said active components are provided. According to an embodiment, said delivery form is selected from the group consisting of tablets, suppositories, capsules, vaporizer cartridges, vaporizer tablets, aerosol cartridges, cigarettes, topical, patches, oil droplets, edibles, beverages and combinations thereof. According to an embodiment, said compartments are configures to contain tablets of multiple compositions, suppositories of multiple compositions, capsules of multiple compositions, vaporizer cartridges of multiple content compositions, aerosol cartridges of multiple content compositions, vaporizer tablets of multiple compositions, cigarettes of multiple compositions, topical of multiple composition, patches of multiple composition, oil droplets of multiple composition, edibles of multiple composition, beverages of multiple composition and combinations thereof.

According to an embodiment, said dispenser comprises at least one control unit. According to an embodiment, said control unit comprises a data processing unit. According to an embodiment, said control unit is configured to control at least one of dispensing unit, vaporizing unit, vaporizing unit heating element, spraying unit and combustion unit, combustion unit heating element. According to an embodiment, said control unit is configured to receive data from at least one of said data input unit, said user feedback unit, said data storing unit and said billing unit. According to an embodiment, said control unit is configured to send data to at least one of said data output unit and said billing unit. According to an embodiment, said control unit is operated via a remote control, wherein said control unit is operated offline, or wherein said control unit is operated by said caregiver. According to an embodiment, said data input unit, said data output unit and/or said feedback input is selected from wire communication, wireless communication and combination thereof. According to an embodiment, said wireless communication is configured to use a wireless protocol, e.g. selected from the group consisting of UPB, INSTEON, Z-Wave, Bluetooth, HomePlug, INSTEON, Wi-Fi and ZigBee. According to an embodiment, said data processing unit, said data storage unit or both comprise at least one of CPU, ROM, RAM and microchip.

According to an embodiment, said dispensing unit is configured to be controlled by said control unit, and to transfer at least one selected cannabis metered dose from a compartment to receiving unit. According to an embodiment, said receiving unit comprises a port or a tray. According to an embodiment, said receiving unit comprises a cup, a syringe or a dropper. According to an embodiment, said metered dose delivery form is selected from tablets, capsules, suppositories, vaporizer tablet or vaporizer cartridge, aerosol cartridges, cigarettes topical, patches, oil droplets, edibles, beverages and combinations thereof and said dispensing unit transfers it to a port, a tray, a cup, a syringe or a dropper, wherefrom it can be collected by said user or by a caregiver.

According to an embodiment, the multi-users cannabis dispenser further comprises at least one cannabis activation unit, wherein said cannabis activation unit is configured to activate said at least one active component in said released metered dose to a selected activated form for said specific user.

According to an embodiment, said cannabis activation unit comprises a heating element, wherein said released metered dose is heated by said heating element and wherein said control unit is further configured to control said heating element to vaporize at least a portion of said at least one active component of said metered dose of said cannabis composition according to selected vaporizing parameters, wherein a vapor of said active component is formed and optionally provided to said specific user. According to an embodiment, said heating unit is configured to be controlled by said control unit, which controls heating time, heating rate minimal temperature and maximal temperature.

According to an embodiment, said cannabis activation unit comprises a spraying element wherein said released metered dose is in a liquid form and said spraying unit is configured to spray at least a portion of said at least one active component of metered dose and wherein said control unit is further configured to control said spraying element wherein a spray of said active component is formed and optionally provided to said specific user.

According to an embodiment, said activation unit comprises a combustion element, wherein said metered dose is combusted by said combustion element and wherein said control unit is further configured to control said combustion element to vaporize at least a portion of said at least one active component of said metered dose of said cannabis composition at selected vaporizing parameters, wherein a vapor of said active component is formed and optionally provided to said specific user. According to an embodiment, said heating unit is configured to be controlled by said control unit, which controls heating time, heating rate minimal temperature and maximal temperature.

According to an embodiment, said activation unit comprises a gas or a liquid input opening, which gas or liquid input opening is configured to introduce a gas a or liquid to said vaporizing unit. According to an embodiment, said opening is configured to be controlled by said control unit.

According to an embodiment, said activating unit comprises a spraying element. According to an embodiment, said spraying element is configured to spray active components of said transferred cannabis metered dose, whereby a spray of said active components is formed and delivered to a user. According to an embodiment, said spraying element is configured to be controlled by said control unit, which controls spraying parameters, such as droplets size and concentration in said spray. According to an embodiment, said vapors, said spray or combinations thereof are delivered to said user via at least one of a mouth piece and an inhaling mask.

According to an embodiment, said dispenser comprises a data input unit. According to an embodiment, said data input unit is configured to receive data and optionally to transfer said data to said control unit. According to an embodiment, said input unit is configured to receive data selected from the group consisting of user identity data, user personal data, user medical data, user licensing data, user billing data, user parameter data and combinations thereof. According to an embodiment, said personal data comprises at least one of age, gender, body weight, user diet, user eating schedule, marriage status and number of children, education, profession, exercising habits, years of experience with cannabis use, types of cannabis serving used in the past, cannabis serving used during the last week, names of caregivers and family members and instructions of said caregivers and/or family members. According to an embodiment, said medical data comprises at least one of past and present illnesses and symptoms, past and present medication used and their doses, sensitivity to particular medications allergies and past surgeries. According to an embodiment, said licensing data comprises at least one of licensed medical cannabis serving composition, licensed serving delivery form and licensed serving medical cannabis dose, and licensed medical cannabis monthly dose. According to an embodiment, said user parameters data comprises at least one of blood pressure, blood oxygen saturation level, heart beating pace, blood glucose concentration, user pain level, user anxiety level, user temperature, user photograph, and user video. According to an embodiment, said input data unit is configured to receive said data manually, via voice or picture recognition, via an identity card or code or via data transfer from a processing unit, such as mobile phone.

According to an embodiment, said dispenser comprises a data input unit, wherein said data input unit is configured to receive user feedback data. According to an embodiment, said dispenser comprises a user feedback unit, which feedback unit is configured to receive user feedback data and optionally to transfer said feedback data to said control unit. According to an embodiment, said feedback data comprises at least one of symptom severity prior to use, symptom severity after use, user adverse effect user satisfaction, user calmness, user ability to operate daily tasks, user social functioning, user sleepiness, user motility, time to reduction or resolving of symptoms, duration of relief in symptoms and combinations thereof. According to an embodiment, said adverse effects are selected from the group consisting of reduction of glucose level, fatigue, weakness, dizziness, deficits in balance, palpitation, tachycardia, digestive disorders including vomiting and/or diarrhea, headache, coughing, increased appetite, impaired memory, impaired concentration, impaired perception, anxiety, psychotic-like effects and combinations thereof.

According to an embodiment, said dispenser comprises a user-billing unit, which billing unit is configured to bill a user.

According to an embodiment, said dispenser comprises at least one user physical parameter reader or user physical parameters collector. According to an embodiment, said user parameter is selected from the group consisting of blood pressure, blood oxygen saturation level, heart beating pace, blood glucose concentration, user pain level, user anxiety level, user temperature, user photograph, user video recording and combinations thereof. According to an embodiment, said dispenser comprises a data output unit configured to send at least one of cannabis use data, user parameters prior to use, user parameters after use and user feedback data. According to an embodiment, said cannabis use data comprises at least one of selected cannabis composition, selected cannabis dose, selected delivery form, selected receiving unit, selected vaporizer heating profile, selected dispensing date and time and connecting and/or disconnecting data from said power source. According to an embodiment, said data output unit is configured to share data with a central medical records processing device. According to an embodiment, said data output unit comprises any device used to send data from a computer to another device or user. According to an embodiment, said data output unit in the form of audio, video, texted data and combinations thereof. According to an embodiment, said data output unit comprises a monitor, projector, speaker, headphone, printer and combinations thereof.

According to an embodiment, said dispenser comprises a vaporizing unit and/or a spraying unit and further comprises an additive input unit, configured to provide a selected additive in a selected amount to be combined with said vapors and/or spray respectively. According to an embodiment, said dispenser comprising an additive input unit, configured to provide a selected additive in a selected amount to be combined with said active components. According to an embodiment, said additive comprises at least one terpene. According to an embodiment, said additive comprising at least one terpene is selected from the group consisting of pinene, limonene, linalool, caryophyllene, caryophyllene oxide, myrcene, humulene, borneol, eucalyptol, terpineol, nerolidol, phytol, geraniol, bisabolol, camphene, beta-amyrin, thujone, citronellol, pulegone, cycloartenol, cymene, sabinene, carene, terpinene, fenchol, isopulegol, guaiol, phellandrene, eudesmol, ocimene, cardinene, elemene, gurjunene, farnesene, friedelin, carvacrol, eugenol, geranyl acetate, camphor, menthol, iso-menthone, neral, gerial, viridiflorol, germacrene, thymol, Menth-2-en-1-ol, farensol, carotol, myrtenol and combinations thereof. According to an embodiment, said additive comprises at least one herbal preparation. According to an embodiment, said additive comprising at least one herbal preparation is selected from the group consisting of extracts of *Acorus, Acorus calamus, Aloe, Ammi visnaga, Angelica arc, Angelica archangelica Radix, Angelica sinensis, Artemisia, Asphalentum ponjabianum—mumio, Astragalus, Atractylodes macrocephala, Avena sativa, Bacopa, Bacopa monnieri, Barosma betulina, Boswellia, Boswellia* spp, *Capsicum* spp, *Caulophyllum thalictroides, Centella, Cimicfuga, Cimicifuga, Cimicifuga (Actaea) racemose, Cinnamomum zeylanicum, Coptis chinensis, Corydalis yanhusuo, Crataegus* spp, *Crataegus* spp. *Curcuma, Curcuma longa, Dioscorea villosa, Dioscorea Villosa* spp, *Echinacea* spp, *Eleutherococcus senticosus, Entella (Hydrocotyl) asiatica, Filipendula ulmaria, Foeniculum, Foeniculum vulgare, Fucus vesiculosus, Galium, Galium, Ganoderma, Ganoderma lucidum, Garcinia, Ginco, Ginco Biloba, Ginseng, Glycyrrhiza glabra, Grifola, grifola frondosa, Gymnema, Harpagophytum procumbens, Humulus, Humulus lupulus, Hydrastis, Hydrastis canadensis, Hypericum, Hypericum perforatum, Iris versicolor, Laminaria, Lavendula officinalis, Lentinula edodes, Leonarous, Leonurus* spp, *Lepidium meyenii, Lepidium meyenii, Lycium, Lycium barbarum, Matricaria, Melissa officinalis, Mentha piperita, Mitaki, Mumio, Olea europea, origanum, Paeonia lactiflora, Panax ginseng, Passiflora, Passiflora incarnata, Paullinia cupana, Paullinia cupana, Peonia, Peumus boldus, Phelodendron amurense, Piscidia, Piscidia erythrina, Rehmania glutinosa, Preparata, Rhamnus purshiana, Rhodiola, Rhodiola rosea, Rosmarinus officinalis, Rozmarinous, Rumex, Salix, Salix alba, Salvia miltiorrhiza, Salvia officinalis, Sambucus nigra, Schisandra chinensis, Scutalleria laterifolia, Scutellaria baicalensis, Silybum marianum, Sophora flavescens, Stachys betonica, Tabebuia impetiginosa, Tanacetum parthenium, Taraxacum* spp. *Radix, Tribulus terrestris, Trifolium pretense, Trigonella foenum graecum, Turnera, Uncaria tomentosa, Valeriana officinalis, Valleriane, Verbena officinalis, vibronum, Viburnum opulus, Viburnum prunifolium, Viscum Albumvitex, Vitex agnus castus, Witania, Zanthoxylum* spp, *Zingiber officinalis* and combinations thereof.

According to an embodiment, said dispenser is configured to generate said metered dose by selecting at least one of said cannabis serving composition, serving delivery form, serving delivery dose size, said additive and said additive amount according to at least one of said user medical data, user personal data, user parameter data and user feedback data. According to an embodiment, said dispenser is configured to generate said metered dose by selecting at least one of said cannabis serving composition, serving delivery form, serving delivery dose size, said additive and said additive amount, wherein selection is done by a caregiver.

According to an embodiment, said dispenser comprises said activation unit and said control unit is configured to control said heating element according to user medical and personal data and according to dispensed metered dose composition.

According to an embodiment, said dispenser comprises at least one of a power storage unit, a display, a voice notification and voice alarm unit, at least one mouth piece, a mouth piece sterilizer, an inhaling mask, a flowmeter, a metered dose content monitor optionally connected to said data output unit and combinations thereof. According to an embodiment, said flowmeter is configured to measure vapors flow rate. According to an embodiment, said power storage unit is selected from the group consisting of battery, capacitor and combinations thereof. According to an embodiment, said voice notification is configured to notify a user of time to get scheduled cannabis metered dose. According to an embodiment, said voice alarm is configured to notify a caregiver of a problem and/or of improper use (or no, when required) of said dispenser.

According to an aspect of some embodiments of the present invention, there is provided a method for dispensing cannabis to multiple users, the method comprising:
(iv) providing a multi-user cannabis dispenser as disclosed herein,
(v) introducing into each of said at least two compartments of said dispenser at least one cannabis composition comprising at least one active-component; and
(vi) providing to said data input unit at least one data input relating to a specific user, wherein said data input is selected from the group consisting of user identity data, user personal data, user medical data, user licensing data, user billing data and user parameter data,
wherein said control unit receives said data input relating to a specific user, data indicating a metered dose of one or more said cannabis compositions to be administered to said specific user and/or configured to receive data relating to a specific cannabis composition, data indicating a metered dose of said specific composition to be administered to said specific user and controls said dispensing unit to release at least one said metered dose.

According to an embodiment, said dispenser comprises a control-unit controlled vaporizing element, and said method comprises providing to the data input unit data for vaporizing parameters; and vaporizing active components of said transferred cannabis metered dose, whereby vapors of said active components are formed and transferred to a user, wherein said vaporizing is controlled by provided data.

According to an embodiment, said dispenser comprises a control-unit controlled spraying element, and said method comprises providing to the data input unit data for spraying parameters; and spraying active components of said transferred cannabis metered dose, whereby spray of said active components is formed and transferred to a user; wherein said spraying is controlled by provided data.

According to an embodiment, said dispenser comprises a control-unit controlled combustion element, and said method comprises providing to the data input unit data for vaporizing parameters; and vaporizing active components of said transferred cannabis metered dose, whereby vapors of said active components are formed and transferred to a user, wherein said vaporizing is controlled by provided data.

According to an embodiment, said dispenser comprises an additive unit, further comprising introducing a selected additive to said additive unit and adding a selected amount of said additive to said selected dispensed metered dose. According to an embodiment, said additive comprises at least one terpene. According to an embodiment, said additive comprises at least one herbal preparation.

According to an embodiment, said cannabis metered dose delivery form is selected from the group consisting of tablets, suppositories, capsules, vaporizer cartridges, vaporizer tablets, aerosol cartridges, cigarettes, topical, patches, oil droplets, edibles, beverages and combinations thereof. According to an embodiment, said cannabis metered dose compositions is selected from the group consisting of at least one of a cannabinoid, a solution of a cannabinoid in a solvent, a cannabis plant material, a cannabis extract, at least one of a terpene, a solution of said extract in a solvent and combinations thereof.

According to an embodiment, said method comprises billing said user according to the selected metered dose dispensed to the user.

According to an embodiment, of said method, said dispensing is remote controlled, said dispensing is operated offline, or said dispensing is operated by an operator or a caregiver.

According to an embodiment, said dispenser is operated in a public place, e.g. a place where users gather, such as a club, a restaurant, a bar or a shopping mall. According to another embodiment, said dispenser is operated in a nursing home or in a hospital, where users are capable of taking care of their needs or are not. According to still another embodiment, said dispenser is operated in a farm or in another location where there are multiple animal users.

According to an embodiment, said dispenser is used by multiple users. According to an embodiment, said users uses said metered dose for recreational purposes, when by himself or herself, or during a social event. According to an embodiment, said metered dose is used as such or combined with another ingestible, e.g. in a beverage, health or energy drink or alcoholic drink. According to an embodiment, said users uses said metered dose for medical purposes, including treating indications, conditions, and/or symptoms such as arthritis, osteoarthritis, arthralgia, joint pain, joint stiffness, diabetes, anorexia, vomiting, nausea, an inflammatory bowel disease including Crohn's disease and ulcerative colitis, dementia, osteoporosis, fatigue, weakness, decreased mental energy, decreased physical energy, dizziness, deficits in balance, itchy skin, pruritus and/or chronic pruritus, stretch marks, skin burn, headache, migraine, weight gain, digestive problem, intestinal disorder, gastrointestinal pain, abdominal pain, pelvic pain, constipation, diarrhea, hot flashes, sweating, difficulty in concentration, weakened immune system, cardiovascular disease, palpitation and tachycardia, psoriasis, infectious conditions, dermatophytes, *Candida, leishmaniasis*, Methycillin-resistant *Staphylococcus aureus* (MRSA), malaria, allergy, fibromyalgia, nociceptive pain, neuropathic pain, pain, arm or leg pain, acne, insomnia and/or sleep disorders, muscle pain, myalgia, spasticity, muscle tension, cramps, spasms, anxiety, irritability, nervousness, restless, stress, depression, mood problem, affect disorders, anger, autism and/or autism spectrum disorder, neurodegenerative diseases, Alzheimer disease, Parkinson disease, Huntington's disease, Dystonia, Amyotrophic Lateral Sclerosis (ALS), multiple sclerosis, Tourette syndrome, Myasthenia Gravis, epilepsy, cancer, inflammatory airway diseases including asthma and/or chronic obstructive pulmonary disease (COPD), addiction, stroke, traumatic brain injury, motor spasm and/or tic, vocal tic, obsessive compulsive disorder (OCD), attention deficit hyperactivity disorder (ADHD), attention deficit disorder (ADD), cerebral palsy (CP), inflammation, oxidative stress, paresthesia, glaucoma and combinations thereof.

According to an embodiment, said dispenser is locked and configured to dispense one metered dose or a selected number of metered doses at a time. According to an embodiment, said dispenser is configured to contain multiple cannabis compositions comprising at least one active component and to operate for days or weeks with no need for often refill. According to an embodiment, operating said dispenser comprises introduction into the dispenser compartments cannabis compositions comprising at least one active component of selected cannabis compositions, of selected dose size and of selected delivery form. According to an embodiment, occasionally, a licensed operator conducts said introduction of cannabis compositions comprising at least one active component to the compartments. According to an embodiment, said dispenser comprises a monitor that monitors the amount of cannabis compositions comprising at least one active component in the various compartments and notifies of a need to refill.

According to an embodiment, said dispenser serves mainly recreational cannabis users. According to an embodiment, in such case, most compartments contain cannabis cigarettes (also referred to as pre-rolls), cartridges and/or tablets for vaporizers and capsules containing preparations to be combined with digestibles. According to an embodiment, the main cannabinoid in such compositions is THC. According to an embodiment, THC content in the metered doses is between 1 mg and 100 mg. According to an embodiment, delivery forms are smoking, inhaling and ingesting (e.g. drinking). According to an embodiment, for delivery forms other than smoking, THC in the metered dose is at least partially decarboxylated. According to an embodiment, the main cannabinoid in such compositions is CBD. According to an embodiment, CBD content in the metered doses is between 1 mg and 100 mg. According to an embodiment, delivery forms are smoking, inhaling and ingesting (e.g. drinking). According to an embodiment, for delivery forms other than smoking, CBD in the metered dose is at least partially decarboxylated.

According to an embodiment, said dispenser input unit identifies said user, receives an order for a metered dose (composition, dose and delivery form) and optionally billing details. According to an embodiment, said input unit transfers the input data to a control unit. According to an embodiment, said control unit confirms that said user is eligible to receive the ordered metered dose (age, license, medical conditions, etc.). If so, the selected order is delivered to preparation.

According to an embodiment, said metered dose is removed from the dispenser and used independently from it. According to an embodiment, the metered dose that is provided to removed from the dispenser and used independently from it is packaged, according to an embodiment the package is marked and the mark includes said user license, metered dose content and prescription to use. According to an alternative embodiment, said dispenser comprises at least one activation unit, e.g. a vaporizing unit, which vaporizes active components of said metered dose to form vapors of said active components and to delivered said vapors to said user, e.g. through a personal mouth piece or through a single-use one. According to an embodiment, said vaporizing unit comprises a heating element and said heating element is controlled by said control unit, which determines heating element operation parameters, such as heating rate, heating maximal temperature and heating time. According to an embodiment, said operation parameters are selected according to the composition of the metered dose, optionally combined with user preference. According to an embodiment, said dispenser is configured so that vapors of a particular metered dose can be shared by multiple users. According to an embodiment, said dispenser is configured to comprise multiple activation units enabling activating multiple metered doses at the same time. According to an embodiment, said dispenser comprises an additive input unit, configured to provide a selected additive in a selected amount to be combined with the metered dose. According to an embodiment, said dispenser comprises an additive input unit, configured to provide a selected additive in a selected amount to be combined with said vapors and/or spray respectively. According to an embodiment, said additive comprises a terpene. According to an embodiment, said dispenser comprises data input unit, control unit, dispensing unit, receiving unit and/or data output unit found only in vaporizers (or other dispensers) that cost at least $400, at least $600, at least $800 or at least $1000.

According to an embodiment, said dispenser serves mainly medical cannabis users. According to another embodiment, said dispenser is operated in a nursing home or in a hospital, where users are capable of taking care of their needs and to move around. According to an embodiment, in such case, said dispenser is fixed to a wall or in a dedicated room. According to an alternative embodiment, or in case where users are not capable of taking care of their needs or to move around, the dispenser is moved between users by an operator, e.g. a caregiver.

According to an embodiment wherein said dispenser serves mainly medical cannabis users, most compartments contain cannabis compositions comprising at least one active component in the form of tablets, suppositories, capsules, vaporizer cartridges, vaporizer tablets and aerosol cartridges. According to an embodiment, the main cannabinoids in such cannabis compositions comprising at least one active component are THC and/or CBD. According to an embodiment, said cannabis compositions comprising at least one active component comprise both THC and/or CBD in weight per weight ratios between moo and 100:1 or between 1:10 and 10:1. According to an embodiment, said cannabinoids are at least partially in decarboxylated form. According to an embodiment, cannabinoids content in said metered doses is typically between 1 mg and 100 mg.

According to an embodiment, prior to said dispensing, data is provided via said data input unit. According to an embodiment, said data comprise at least one of user identity data, user personal data, user medical data, user licensing data, user billing data and user parameter data. According to various embodiment, said data is provided in advance (for example on user admission to nursing home or hospital), read from a dedicated card or introduced manually by the operator or caregiver.

According to an embodiment, user physical parameters are read or collected prior to said dispensing. According to an embodiment, user physical parameters are read or collected during and/or following to said dispensing. According to an embodiment, said dispenser comprises at least one user physical parameter reader or user physical parameters collector. According to an embodiment, said user parameter is selected from the group consisting of blood pressure, blood oxygen saturation level, heart beating pace, blood glucose concentration, user pain level, user anxiety level, user temperature, user photograph, user video recording and combinations thereof. According to an embodiment, user physical parameters are provided to said data input unit.

According to an embodiment, a selected medical cannabis dose is dispensed from a selected compartment. According to an embodiment, wherein said dispensing is controlled by said control unit according to the provided data. According to an embodiment, said control unit first confirms that said user is eligible to receive the ordered metered dose, e.g. is licensed to do so. According to an embodiment, said control unit confirms that the user medical condition is suitable for such use based on input medical data and optionally also based on recorded physical parameters. According to an embodiment, a caregiver, e.g. a physician, has the possibility of blocking the delivery, including by remote data input.

According to an embodiment, said data processing device is configured to block processing or to limit it as required, e.g. by the history of administrating or by instruction of a treating person, e.g. a physician. According to an embodiment, based on such data, the control unit selects dispensing time.

According to an embodiment, if approved, a selected medical cannabis metered dose is dispensed. According to an embodiment, selected metered dose composition, dose and delivery form are controlled by said control unit according to user personal data, medical condition and measured physical parameters. According to an embodiment, user indication, symptom and conditions determine the metered dose composition, e.g. THC/CBD ratio, content of other cannabinoids and content of terpenes, based on existing knowledge for optimal treatment. According to an embodiment, metered dose composition is also determined by user age with a preference for low proportions of THC in case of treating infants and children. According to an embodiment, metered dose is determined by similar parameters, e.g. by user body weight. According to an embodiment, the nature and dose of other medications provided to the user affect selected metered dose composition, selected metered dose amount and/or metered dose time. According to another embodiment, metered dose composition, metered dose amount, metered dose delivery form and/or metered dose time is selected according to user feedback, e.g. dose is reduced in case the user reported an adverse effect, such as dizziness.

According to an embodiment, the delivery method is selected based on input data, e.g. inhalation of active component vapors in case of acute pain (due to short onset time) and slow-release tablets for chronic pain. According to an embodiment, said metered dose is removed from the dispenser and used independently from it, e.g. as in the case of tablets, capsules or suppositories. According to an embodiment, said metered dose is removed from the dispenser and used in a separate vaporizer or spray generator. According to an alternative embodiment, said dispenser comprises at least one activation unit, e.g. a vaporizing unit and/or a spraying unit, which form vapors of active components and/or a spray of the active components and delivers them to said user, e.g. through a personal mouth piece or through a single-use one. Alternatively, vapors or spray are delivered into an inhalation mask. According to an embodiment, said dispenser comprises a vaporizing unit, said vaporizing unit comprises a heating element and said heating element is controlled by said control unit, which determines heating element operation parameters, such as heating rate, heating maximal temperature and heating time. According to an embodiment, said operation parameters are selected according to the composition of the metered dose and/or according to user personal data, medical data, physical parameters and/or prior feedback.

According to an embodiment, said dispenser comprises an additive input unit, configured to provide a selected additive in a selected amount to be combined with said metered dose and/or vapors and/or spray. According to an embodiment, said additive comprises a terpene. According to an embodiment, said additive comprises an herbal preparation. According to an embodiment, said dispenser comprises data input unit, control unit, dispensing unit, receiving unit and/or data output unit found only in vaporizers (or other dispensers) that cost at least $400, at least $600, at least $800 or at least $1000. According to an embodiment, said dispenser comprises data input unit, control unit, dispensing unit, receiving unit, feedback unit and/or data output unit that are too complicated to be operated optimally by some of users, e.g. to their physical conditions or age.

According to an embodiment, said dispenser comprises a data output unit which unit shares at least one of medical cannabis use data, user parameters prior to use, user parameters after use, user feedback and user adverse effects. According to an embodiment, said data is shared with a central medical records processing device. According to an embodiment, said shared data is used for improving the service provided to the user, e.g. by designing new metered dose composition, improved selection of metered dose composition, metered dose amount or metered dose delivery form, better selection of dispensing time, etc.

EXAMPLES

Figure 1:
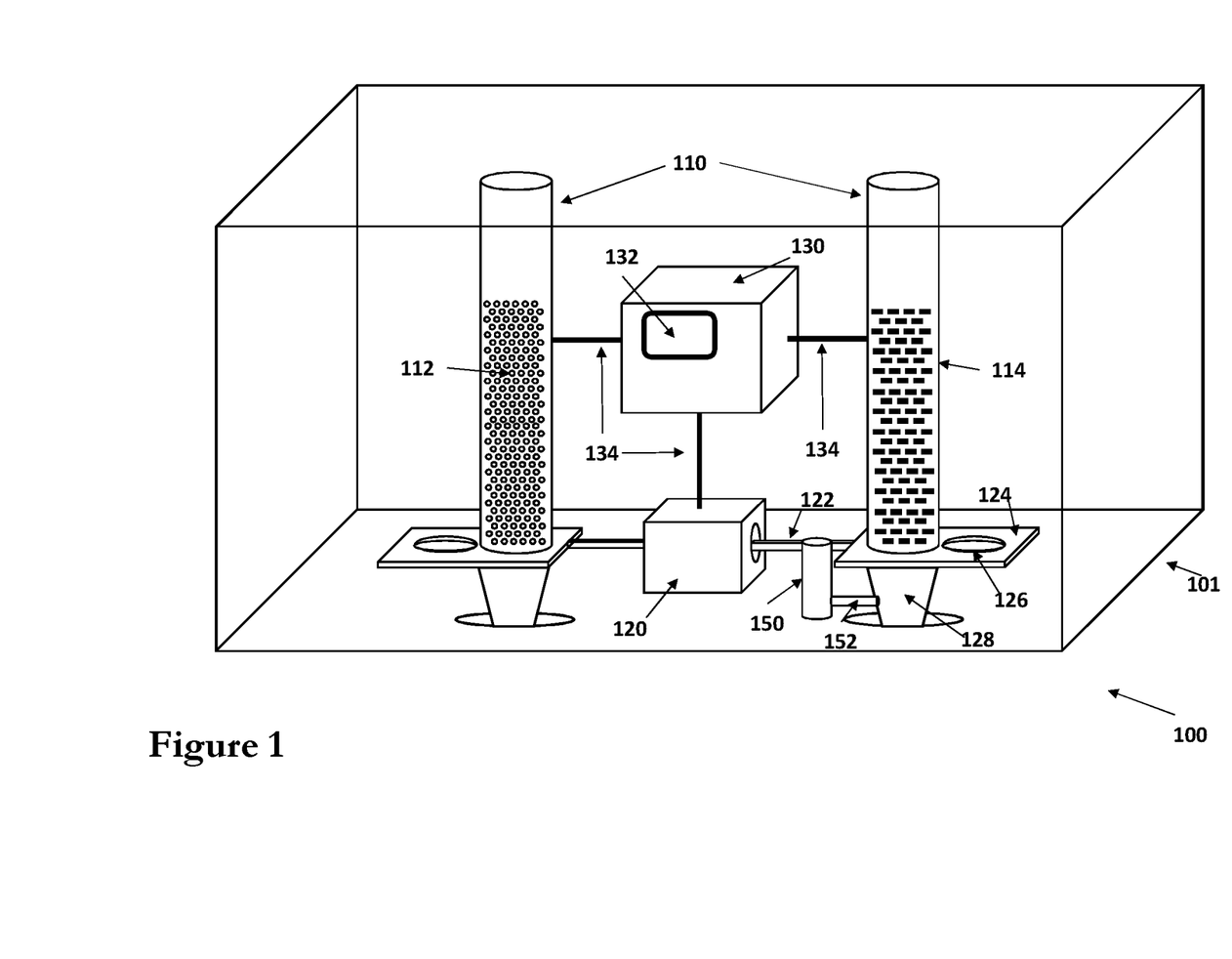
FIG. 1 schematically illustrates a multi-user cannabis dispenser, in accordance with an exemplary embodiment of the present invention.

An exemplary multi-user cannabis dispenser is schematically shown in FIG. 1 (100). The exemplary multi-user cannabis dispenser comprises a vessel (101), which vessel comprises two compartments (110) each compartment being configured to contain therein at least one cannabis composition comprising at least one active component (112,114). The exemplary multi-user cannabis dispenser comprises a dispensing unit (120) associated with the at least one compartment (110) and configured to controllably release from the compartments (110) a metered dose of the composition (112,114) by moving a plate (124) connected to a rod (122), the plate (124) having a hole (126) provided therein, wherein moving the plate (124) opens the compartment (110) causing the dispensing of cannabis composition comprising at least one active component (112, 114) to a dispensing funnel (128). The exemplary multi-user cannabis dispenser comprises a control unit (130), comprising a data input unit (132) configured to receive data relating to a specific user, data indicating a metered dose of one or more cannabis compositions to be administered to the specific user and/or configured to receive data relating to a specific cannabis composition, data indicating a metered dose of the specific composition to be administered to the specific user, the control unit (130) is connected to the dispensing unit (120) and to the compartments (110) by connections (134). The multi-user cannabis dispenser may optionally further comprise an additive input unit (150), configured to provide a selected additive in a selected amount (152) to be combined with the metered dose.

In an exemplary use of the multi-user cannabis dispenser of FIG. 1, the two compartments (110) located inside the vessel (101) are each provided with at least one cannabis composition comprising at least one active component. According to some embodiments, the cannabis composition comprising at least one active component contained within the compartments can be a ground plant, a solid, a liquid or in wax form (or any combination thereof) in a bulk form or pre divided into individual doses, with or without packaging. The compartments (110) are configured to contain the cannabis composition comprising at least one active component in a way that enable a suitable storage time of at least 6 months. In FIG. 1. cannabis compositions comprising at least one active component (112, 114) differ from each other in at least one of; form, size, or active component concentration or kind. According to some embodiments, connections (134) enable data input relating to the cannabis compositions to control unit (130). In addition the control unit (130) comprises a data input unit (132) configured to receive data relating to a specific user, data indicating a metered dose of one or more the cannabis compositions to be administered to the specific user and/or configured to receive data relating to a specific cannabis composition, data indicating a metered dose of the specific composition to be administered to the specific user. The data input unit can obtain the data directly from the operator, or by connection of a communication device to a remote server (not shown). The control unit is configured to receive data from the user such as, but not limited to, feedback or physical parameters (not shown). In addition the control unit (130) can use the communication device to transfer any data received from the user or the multi-user cannabis dispenser. A user, when approaching the multi-user cannabis dispenser can use the data input unit (132) to identify himself, the control unit (130) then checks that the user is authorized. When the user is identified to the data input unit (132) as being authorized, the control unit (130) controls the dispensing unit (120) to dispense the metered dose of cannabis compositions comprising at least one active component in accordance with any one of: user parameter, user feedback parameters or available specific cannabis composition.

Figure 2:
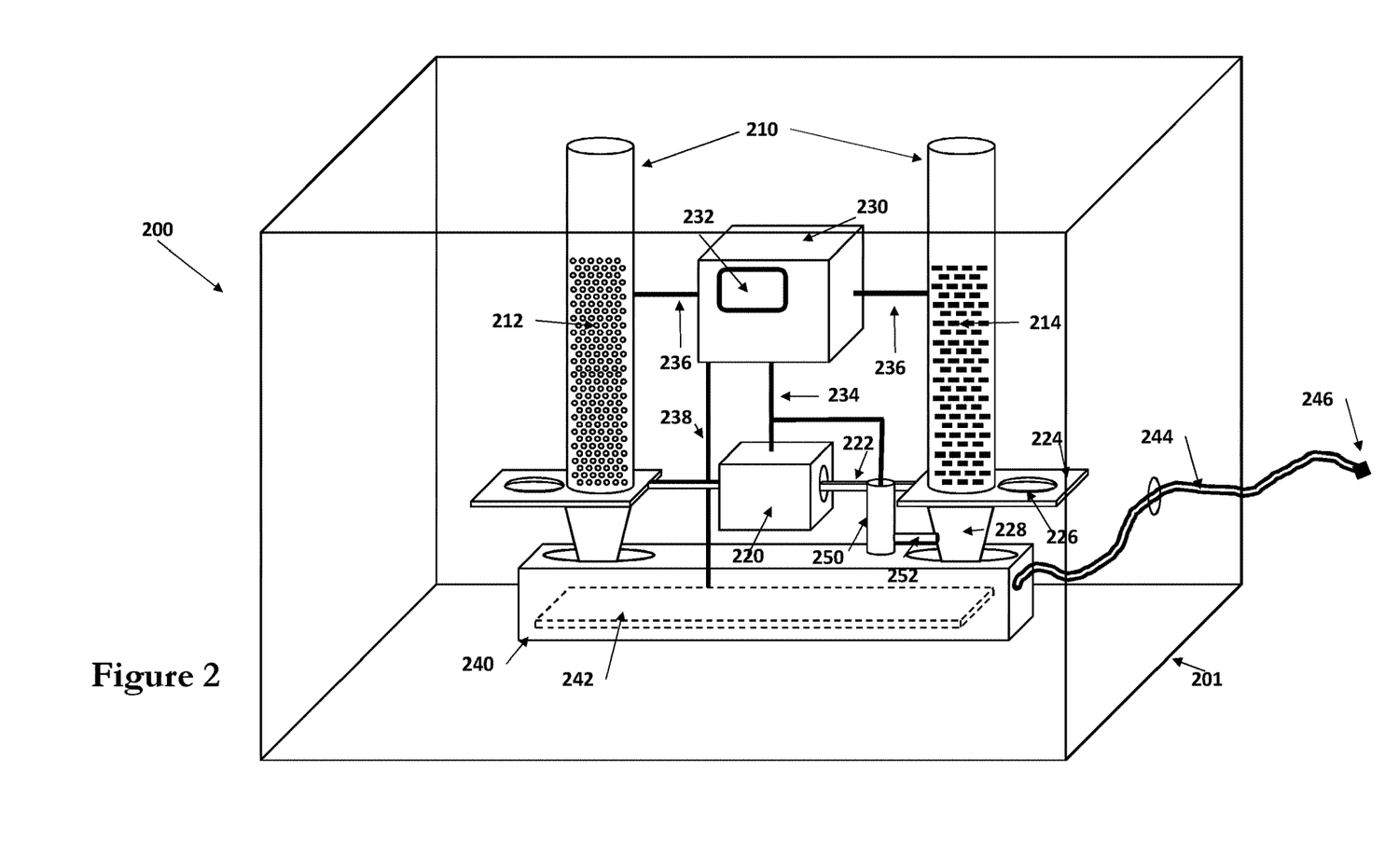
FIG. 2 schematically illustrates a multi-user cannabis dispenser, in accordance with an exemplary embodiment of the present invention.

A further exemplary multi-user cannabis dispenser is schematically shown in FIG. 2 (200). The exemplary multi-user cannabis dispenser comprises a vessel (201), which vessel comprises two compartments (210) each compartment being configured to contain therein at least one cannabis composition comprising at least one active component (212,214). The exemplary multi-user cannabis dispenser comprises a dispensing unit (220) associated with the at least one compartment (210) and configured to controllably release from the compartments (210) a metered dose of the composition (212,214) by moving the plate (224) connected to a rod (222), the plate (224) having a hole (226) provided therein, wherein moving the plate (224) opens the compartment (210), causing the dispensing of a metered dose of a cannabis composition comprising at least one active component (212, 214) to the dispensing funnel (228) into an activation unit (240) that comprises at least one activation element (242). The multi-user cannabis dispenser may optionally further comprise an additive input unit (250), configured to provide a selected additive in a selected amount (252) to be combined with the metered dose before activation in the activation unit (240). The exemplary multi-user cannabis dispenser comprises a control unit (230), comprising a data input unit (232) configured to receive data relating to a specific user, data indicating a metered dose of one or more cannabis compositions to be administered to the specific user and/or configured to receive data relating to a specific cannabis composition, data indicating a metered dose of the specific composition to be administered to the specific user, the control unit (230) is connected to the dispensing unit (220) and to the additive input unit (250) by the connection (234), to the compartments (210) by connections (236) and to the activation unit (240) by connection (238). A tube (244) and a replaceable mouthpiece (246) are connected to the activation unit (240) and extend out of the vessel (201).

In an exemplary use of the multi-user cannabis dispenser of FIG. 2, the two compartments (210) located inside the vessel (201) are each provided with at least one cannabis composition comprising at least one active component. According to some embodiments, the cannabis composition comprising at least one active component provided within the compartments can be a ground plant, a solid, a liquid or in wax form (or any combination thereof) in a bulk form or pre divided into individual doses, with or without packaging. The compartments (210) configured to obtain the cannabis composition comprising at least one active component in a way that enables a suitable storage time of at least 6 months. In FIG. 2. cannabis compositions comprising at least one active component (212, 214) differ from each other in at least one of; form, size, or active component concentration or kind. According to some embodiment connections (236) enable data input of the cannabis compositions to control unit (230). In addition the control unit (230) comprises a data input unit (232) configured to receive data relating to a specific user, data indicating a metered dose of one or more the cannabis compositions to be administered to the specific user and/or configured to receive data relating to a specific cannabis composition, data indicating a metered dose of the specific composition to be administered to the specific user. The data input unit can obtain the data directly from the operator, or by connection of communication device to a remote server (not shown). The control unit is configured to receive data from the user such as, but not limited to, feedback or physical parameters (not shown). In addition, the control unit (230) can use the communication device to transfer any data received from the user or the multi-user cannabis dispenser. A user when approaching the multi-user cannabis dispenser can use the data input unit (232) to identify himself, the control unit (230) then checks that the user is authorized. When the user is identified to the data input unit (232) as being authorized, the control unit (230) controls the dispensing unit (220) to dispense the metered dose of cannabis compositions comprising at least one active component in accordance of any one of: user parameter, user feedback parameters or available specific cannabis composition. if required, adding, an additive from additive input unit (250) to the metered dose, before dispensing the dose to the activation unit. the control unit (230) control the metered dose by activation element (242) by a selected profile set according to the input user data and composition data to generate a smoke or fume that can be inhale by user through tube (244) and replaceable mouthpiece (246).

Figure 3:
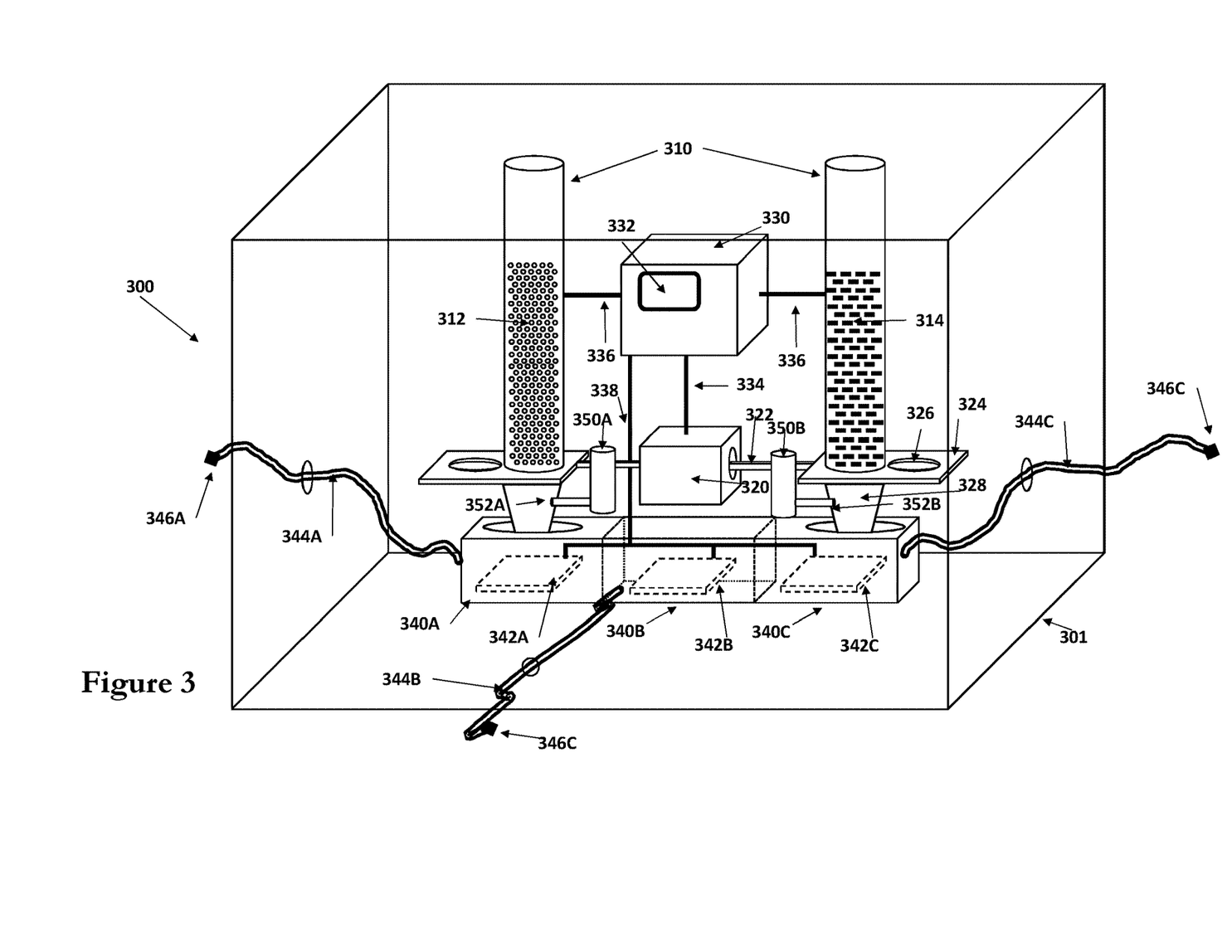
FIG. 3 schematically illustrates a multi-user cannabis dispenser, in accordance with an exemplary embodiment of the present invention.

A further exemplary multi-user cannabis dispenser is schematically shown, in FIG. 3 (300). The exemplary multi-user cannabis dispenser comprises a vessel (301), which vessel comprises two compartments (310) each compartment being configured to contain therein at least one cannabis composition comprising at least one active component (312,314). The exemplary multi-user cannabis dispenser comprises a dispensing unit (320) associated with the at least one compartment (310) and configured to controllably release from the compartments (310) a metered dose of the composition (312,314) by moving the plate (324) connected to a rod (322), the plate (324) having a hole (326) provided therein, wherein moving the plate (324) opens the compartment (310) causing the dispensing of a metered dose of a cannabis composition comprising at least one active component (312, 314) to the dispensing funnel (328), into the activation unit (340) that comprises at least one activation element (343) The multi-user cannabis dispenser may optionally further comprise an additive input unit (350), configured to provide a selected additive in a selected amount (352) to be combined with the metered dose before activation in the activation unit (340). The exemplary multi-user cannabis dispenser comprises a control unit (330), comprising a data input unit (332) configured to receive data relating to a specific user, data indicating a metered dose of one or more cannabis compositions to be administered to the specific user and/or configured to receive data relating to a specific cannabis composition, data indicating a metered dose of the specific composition to be administered to the specific user, the control unit (330) is connected to the dispensing unit (320) and to the additive input unit (350) by the connection (334), to the compartments (310) by connections (336) and to the activation unit (340) by connection (338). A tube (344) and a replaceable mouthpiece (346) are connected to the activation unit (340) and extend out of the vessel (301).

In an exemplary use of the multi-user cannabis dispenser of FIG. 3, the two compartments (310) located inside the vessel (301) are each provided with at least one cannabis composition comprising at least one active component. According to some embodiments, the cannabis composition comprising at least one active component provided within the compartments can be a ground plant, a solid, a liquid or in wax form (or any combination thereof) in a bulk form or pre divided into individual doses, with or without packaging. The compartments (310) configured to contain the cannabis composition comprising at least one active component in a way that enables a suitable storage time of at least 6 months. In FIG. 3. cannabis compositions comprising at least one active component (312, 314) differ from each other in at least one of; form, size, or active component concentration or kind. According to some embodiment connections (336) enable data input relating to the cannabis compositions to control unit (330). In addition the control unit (330) comprising a data input unit (332) configured to receive data relating to a specific user, data indicating a metered dose of one or more cannabis compositions to be administered to the specific user and/or configured to receive data relating to a specific cannabis composition, data indicating a metered dose of the specific composition to be administered to the specific user. The data input unit can get the date directly from the operator, or by connection of communication device to remote server (not shown). The control unit is configured to receive data from the user such as, but not limited to, feedback or physical parameters (not shown). In addition, the control unit (330) can use the communication device to transfer any data received from the user or the multi-user cannabis dispenser. A user when approaching the multi-user cannabis dispenser can use the data input unit (332) to identify himself, the control unit (330) then checks that the user is authorized. When the user is identified to the data input unit (332) as being authorized, the control unit (330) controls the dispensing unit (320) to dispense the metered dose of cannabis compositions comprising at least one active component in accordance with any one of: user parameter, user feedback parameters or available specific cannabis composition. if required, adding, an additive from additive input unit (350) onto the metered dose, before dispensing the dose to the activation unit (340). the control unit (330) control the metered dose by activation element (342) by a selected profile set according to the input user data and composition data to generate a smoke or fume that can be inhale by user through tube (344) and replaceable mouthpiece (346).

Figure 4:
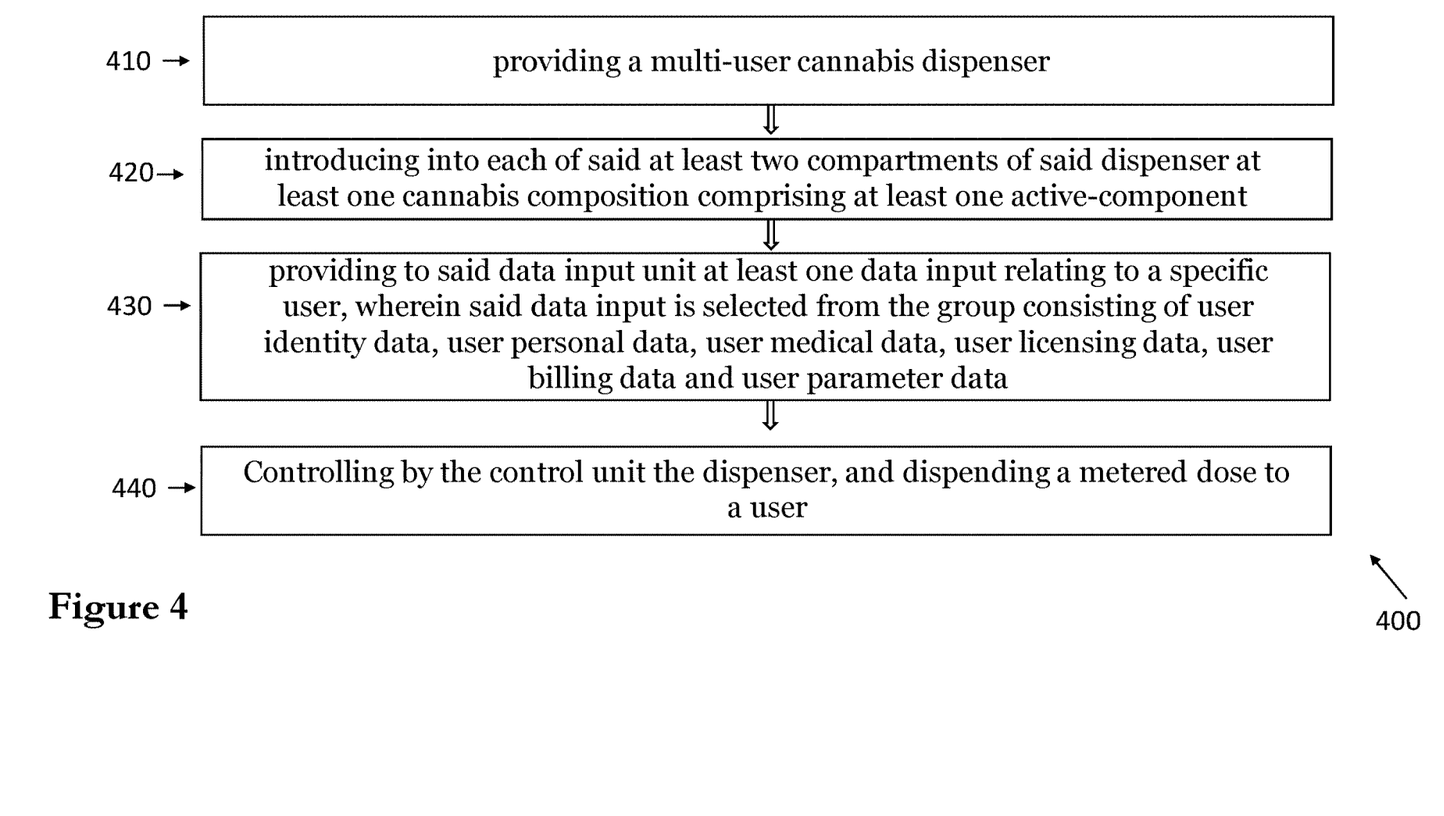
FIG. 4 is a flow chart showing a method, in accordance with an exemplary embodiment of the present invention.

FIG. 4 shows a flow chart of a method, in accordance with an exemplary embodiment of present invention (400). The method comprises: providing a multi-user cannabis dispenser (410) according to any one of FIGS. 1 to 3; introducing into each of said at least two compartments of said dispenser at least one cannabis composition comprising at least one active-component (420); providing to said data input unit at least one data input relating to a specific user, wherein said data input is selected from the group consisting of user identity data, user personal data, user medical data, user licensing data, user billing data and user parameter data (430); and Controlling by the control unit the dispenser, and dispensing a metered dose to a user (440).

Figure 5:
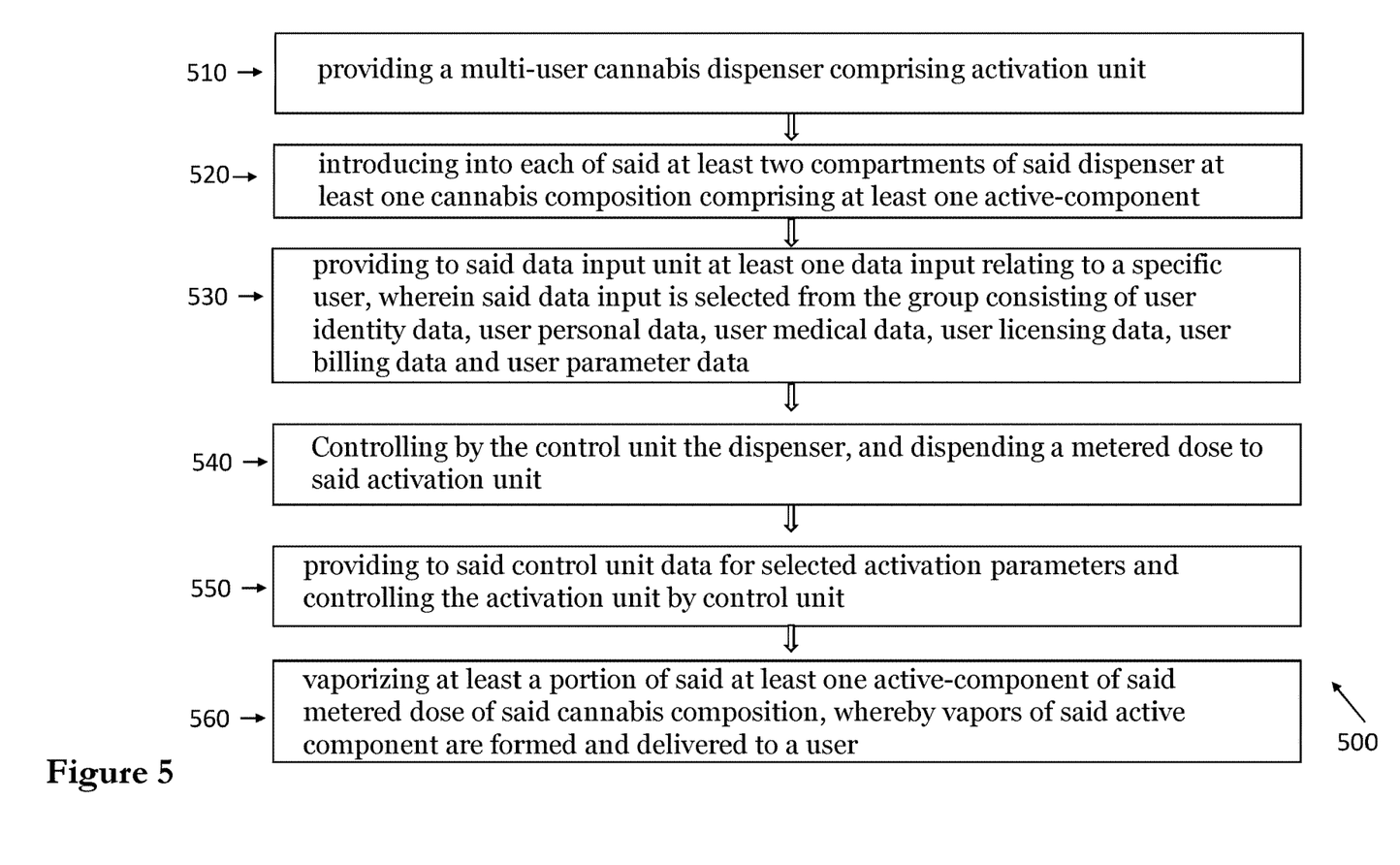
FIG. 5 is a flow chart showing a method, in accordance with additional exemplary embodiment of the present invention.

FIG. 5 shows a flow chart of a method, in accordance with exemplary embodiment of present invention (500). The method comprises: providing a multi-user cannabis dispenser according to any one of FIG. 2 or 3, comprising an activation unit (510); introducing into each of said at least two compartments of said dispenser at least one cannabis composition comprising at least one active-component (520); providing to said data input unit at least one data input relating to a specific user, wherein said data input is selected from the group consisting of user identity data, user personal data, user medical data, user licensing data, user billing data and user parameter data (530); Controlling by the control unit the dispenser, and dispensing a metered dose to said activation unit (540); providing to said control unit data for selected activation parameters and controlling the activation unit by control unit (550); and vaporizing at least a portion of said at least one active-component of said metered dose of said cannabis composition, whereby vapors of said active component are formed and delivered to a user (560).

Thus, the scope of the invention shall include all modifications and variations that may fall within the scope of the attached claims. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A multi-users cannabis dispenser comprising:
   (i) a vessel comprising at least two compartments, each compartment being configured to contain therein at least one cannabis composition comprising at least one active component;
   (ii) at least one dispensing unit associated with said at least two compartments, wherein said at least one dispensing unit is configured to controllably release from said compartments a metered dose of said composition contained therein;
   (iii) a control unit comprising a data input unit configured to receive user identity data relating to a specific user, and data indicating a metered dose of one or more said cannabis compositions to be administered to said specific user, wherein said control unit is further configured to control the at least one dispensing unit to release at least one said metered dose of cannabis composition to each of the multiple users substantially simultaneously; and
   (iv) at least one cannabis activation unit configured to activate said at least one active component in said released metered dose to a selected activated form for said specific user, wherein:
  (a) one of said at least one cannabis activation unit comprises a spraying element wherein said released metered dose is in a liquid form and said spraying element is configured to form a spray from at least a portion of said liquid, and wherein said control unit is further configured to control said spraying element, and/or
  (b) one of said at least one cannabis activation unit comprises a combustion element comprising a combustion heating element configured to combust said released metered dose of said cannabis composition to produce a smoke comprising at least a portion of said at least one active component of said cannabis composition, and wherein said control unit is further configured to control said combustion element.

2. The multi-users cannabis dispenser of claim 1, wherein said at least one cannabis composition is provided in a selected dose size and/or selected delivery form.

3. The multi-users cannabis dispenser of claim 1, wherein said at least one cannabis activation unit further comprises another at least one cannabis activation unit comprising a vaporizing heating element, wherein said released metered dose is heated by said vaporizing heating element and wherein said control unit is further configured to control said vaporizing heating element to vaporize at least a portion of said at least one active component of said metered dose of said cannabis composition according to selected vaporizing parameters, wherein a vapor of said active component is formed.

4. The multi-users cannabis dispenser of claim 1, wherein said data input unit is configured to receive data comprising at least one user parameter selected from the group consisting of user identity data, user personal data, user physical data, user medical data, user licensing data, user billing data and user parameter data or combinations thereof.

5. The multi-users cannabis dispenser of claim 1, further comprising at least one unit selected from the group consisting of:
  (i) a user feedback unit configured to receive feedback data of a user, wherein said feedback data comprises at least one selected from the group consisting of symptom severity prior to use, symptom severity after use and adverse effect of user;
  (ii) user-billing unit configured to provide a bill related to a user; and
  (iii) at least one user physical parameter reader configured to obtain a physical parameter from a user.

6. The multi-users cannabis dispenser of claim 1, wherein said at least one cannabis composition comprises at least one selected from the group consisting of a cannabinoid, a solution of a cannabinoid in a solvent, a cannabis plant material, a cannabis extract, at least one terpene, a solution of said extract in a solvent and combinations thereof.

7. The multi-users cannabis dispenser of claim 1, wherein said metered dose is selected from the group consisting of tablets, suppositories, capsules, vaporizer cartridges, vaporizer tablets, aerosol cartridges, cigarettes, topicals, patches, oil droplets, edibles, beverages and combinations thereof.

8. The multi-users cannabis dispenser of claim 1, wherein each of said at least two compartments is independently configured to contain a dose form of a cannabis composition selected from the group consisting of tablets, suppositories, capsules, vaporizer cartridges, vaporizer tablets, aerosol cartridges, cigarettes, topicals, patches, oil droplets, edibles, beverages and combinations thereof.

9. The multi-users cannabis dispenser of claim 3, wherein said control unit is configured to control said vaporizing heating element according to at least one selected from the group of a data input comprising user medical and/or personal data, said metered dose data or both.

10. The multi-users cannabis dispenser of claim 9, wherein said user medical data comprises at least one selected from the group consisting of user medical condition, user medical parameters data, and user medication protocol.

11. The multi-users cannabis dispenser of claim 1, wherein said received data relating to a specific user is a property or sensed parameter selected from the group consisting of age, gender, blood pressure, blood oxygen saturation level, heart rate, blood glucose concentration, user pain sensitivity, user anxiety level, user temperature, user photograph, user video recording, user EEG data, and combinations thereof.

12. The multi-users cannabis dispenser of claim 1, wherein said received data relating to a specific cannabis composition comprises at least one of selected cannabis batch ID, selected cannabis composition, selected cannabis dose, selected delivery form, selected activation unit, selected heating profile, selected dispensing date and time of dispensing and combinations thereof.

13. The multi-users cannabis dispenser of claim 1, wherein said control unit is configured to communicate with at least one selected from the group consisting of a supervisor and a medical server, wherein said supervisor and/or said medical server can receive data and operate said control unit.

14. The multi-users cannabis dispenser of claim 1, further comprising an additive input unit, configured to provide a selected additive in a selected amount to be combined with said metered dose.

15. The multi-users cannabis dispenser of claim 1, further comprising at least one selected from the group consisting of a power storage unit, a display, a voice notification and voice alarm unit, at least one mouth piece, a mouth piece sterilizer, an inhaling mask, a flowmeter, a metered dose content monitor and combinations thereof.

16. A method for dispensing cannabis to multiple users, the method comprising:
  (i) providing a multi-user cannabis dispenser according to claim 1,
  (ii) introducing into each of said at least two compartments of said dispenser at least one cannabis composition comprising at least one active-component; and
  (iii) providing to said data input unit at least one data input relating to a specific user, wherein said data input is selected from the group consisting of user identity data, user personal data, user medical data, user licensing data, user billing data and user parameter data,
  wherein said control unit receives said data input relating to a specific user, data indicating a metered dose of one or more said cannabis compositions to be administered to said specific user and/or configured to receive data relating to a specific cannabis composition, data indicating a metered dose of said specific composition to be administered to said specific user and controls said dispensing unit to release at least one said metered dose.

* * * * *